United States Patent [19]

Walch et al.

[11] 4,075,093

[45] Feb. 21, 1978

[54] PROCESS OF SEPARATING CITRIC ACID AND/OR ISOCITRIC ACID OR THEIR SALTS FROM AQUEOUS SOLUTIONS

[75] Inventors: Axel Walch; Albrecht Klimmek, both of Frankfurt am Main; Klaus Wollmann, Eschhofen, all of Germany

[73] Assignee: Joh. A. Benckiser GmbH, Ludwigshafen (Rhine), Germany

[21] Appl. No.: 625,140

[22] Filed: Oct. 23, 1975

[30] Foreign Application Priority Data

Oct. 25, 1974 Germany ............................ 2450670

[51] Int. Cl.$^2$ .............................................. B01D 13/00
[52] U.S. Cl. ............................... 210/23 H; 210/500 M
[58] Field of Search ................. 210/23 H, 22, 500 M; 195/36, 47, 31; 426/51

[56] References Cited

U.S. PATENT DOCUMENTS

| 3,004,904 | 10/1961 | Gregor et al. | 204/180 |
|---|---|---|---|
| 3,228,876 | 1/1966 | Mahon | 210/22 |
| 3,228,877 | 1/1966 | Mahon | 210/22 |
| 3,342,729 | 9/1967 | Strand | 210/23 H |
| 3,544,455 | 12/1970 | Adams et al. | 210/23 H |
| 3,673,084 | 6/1972 | King et al. | 210/23 H |
| 3,723,309 | 3/1973 | Bridgeford | 210/22 |
| 3,750,735 | 8/1973 | Chiang et al. | 210/23 X |

Primary Examiner—Frank A. Spear, Jr.
Assistant Examiner—E. Rollins Cross
Attorney, Agent, or Firm—Erich M. H. Radde

[57] ABSTRACT

The process of separating citric acid and/or isocitric acid and their salts from aqueous solutions containing said acids or their salts, and especially from fermentation solutions, consists in contacting said solutions under pressure with a permselective membrane. The material composing said membrane has introduced thereinto acid or basic groups so as to yield membranes of predetermined swelling power. Preferred membranes are those consisting of polyimide or polyamide polycondensation products which are modified by acid or basic groups, of polysulfones modified by acid groups, or of vinyl polymers modified by acid or basic groups. Adjustment of the starting solutions to a pH lower than 3.0 is advantageously effected by means of polyvinylsulfonic acid.

15 Claims, No Drawings

PROCESS OF SEPARATING CITRIC ACID AND/OR ISOCITRIC ACID OR THEIR SALTS FROM AQUEOUS SOLUTIONS

BACKGROUND OF THE INVENTION (1) Field of the Invention

The present invention relates to a novel and highly effective process of recovering, separating, and concentrating citric acid and/or isocitric acid and their salts from aqueous solutions and more particularly from fermentation solutions, thereby separating said acids and their salts from other organic compounds and inorganic salts.

(2) Description of the Prior Art

For solving many problems of separating compounds from each other, there have proved to be especially effective separation processes which utilize a pressure gradient as effective force. Such processes make use of porous and/or semipermeable membranes, as used, for instance, in ultrafiltration and reverse osmosis. There are also known, for instance, processes for reclaiming and purifying certain specific waste waters or sewage, for desalinifying seawater, as well as a number of industrially performed processes for concentrating, isolating, or purifying various types of different compounds. See, for instance, "CZ-CHEMIETECHNIK" vol. 2 (1973), pp. 7 – 11.

By ultrafiltration there are separated at an operating pressure of 7 bars preferably colloidal particles especially according to their particle size (of a diameter between 10° and $10^2$nm) by means of microporous membranes. In contrast thereto hyperfiltration cannot be explained as a simple filtration process. The principle of hyperfiltration which today is generally accepted and which is characterized by the synonym "reverse osmosis" is the reversal of the tendency to cause osmotic dilution on semi-permeable membranes by means of a pressure difference. In this case at least the osmotic pressure difference ($\Delta \pi$) is to be overcome. The model of solution and diffusion as it has been described by H. Yasuda and C. E. Lamaze, Office of Saline Water, "Research and Development Progress Report" No. 473, September 1969, has become generally accepted as a theoretical basis for the transport mechanism and thus also as a basis for the membrane concept. This model takes into account more particularly the correlation between the molecular structure of the polymer membrane material and its separating behavior or effect.

The best known semi-permeable membranes as they are used most frequently in actual operation at the present time consist of cellulose derivatives. Recently, however, other plastic materials such as, for instance, polyacrylic or, respectively, polymethacrylic derivatives, polyamides, and the like, have been employed as membrane material. In these cases a distinction is made between homogeneous and asymmetric membranes in accordance with membrane morphology. The general trend in connection with separation processes using membranes aims at investigations to produce membranes of optimum selectivity for a specific predetermined separation problem.

Thus membranes for pervaporation which are suitable for selective separation of water from aqueous starting mixtures with organic and inorganic dissolved constituents, are known. They consist of an organic polymer having anionic groups which may also contain cationic groups. But according to the inventions to be mentioned in this connection by example (see, for instance, German Published applications Nos. 2,129,723 and 2,129,734), the use of a liquid phase on both sides of the membrane is impracticable because such membranes require for this purpose pressures up to 1,000 bars. Inorganic salts are not to be separated in this manner in accordance with this problem. Thus such membranes are useless for solving the problem upon which the present invention is based.

Selectively permeable membranes are described in German Published application No. 2,051,631. Such membranes consist of copolymers which contain at least 50% of hydrophilic, non-ionic groups, above all hydroxyl groups while the remainder comprises basic or carboxyl groups— containing units. These copolymers are, as stated, more selective when used as ion exchange membranes, as proved on the example of sodium ions $Na^+$ and calcium ions $Ca^{++}$. Data regarding the selectivity properties of these membranes in relation to mixtures of polycarboxylic acids and/or their salts and inorganic monovalent or, respectively, polyvalent anions, however, are not given in the published application.

Membranes with selective permeability which consist of vinyl copolymers and which are synthesized from three or more monomers, are mentioned in German Published application No. 2,044,509. Cross-linking with known bifunctional monomers is also mentioned therein. The selectivity of such membranes, however, has been proved only for the system sodium chloride — water.

German Published application No. 2,027,698 discloses a process for purifying aqueous itaconic acid solutions by reverse osmosis. Polyamides and cellulose esters are listed as membrane materials. According to this application working up a citric acid solution, in place of the itaconic acid solution, has also been tried. However, it was found that the selectivity in this case is very unsatisfactory and that the membranes are not suitable for this purpose.

SUMMARY OF THE INVENTION

It is one object of the present invention to provide a simple and effective process of selectively separating citric acid or citric acid salts from solutions containing same and especially from solutions obtained on producing same, from impurities, and to produce a concentrated solution of citric acid or, respectively, its salts for further processing.

Another object of the present invention is to provide highly effective permselective membranes, i.e. membranes of selective permeability which are useful in said separation process.

Still another object of the present invention is to provide a process of producing such permselective membranes for separating citric acid or its salts from its impurities.

Other objects of the present invention and advantageous features thereof will become apparent as the description proceeds.

As is known, citric acid is to the most part produced on a large industrial scale by fermentation of carbohydrates or hydrocarbons whereby a fermentation liquor or broth which contains in addition to citric acid or, recpectively, citrates as main components, sugars, unfermented carbohydrates, proteins, dyestuffs, and inorganic salts. Citric acid, however, must be isolated in a highly purified quality for most of its use. When using well known processing methods, a considerable technical expenditure is required and frequently losses in citric acid and considerable environmental problems are encountered.

The process according to the present invention of separating citrates or, respectively, citric acid and/or isocitric acid from aqueous solutions and especially from fermentation solutions from accompanying impurities and of concentrating such solutions is characterized by using membranes of selective permeability, the structural material of which is modified by the introduction of acid groups up to a swelling power of between about 5% and about 25%, by volume, or by introducing basic groups into their molecule up to a swelling power of between about 3% and about 15%, by volume. Such permselective membranes are used within a pH-range of about 1.0 to about 8.0 and within a pressure range of about 5 bars to about 100 bars.

According to the present invention various methods of separating and concentrating citrates or, respectively, citric acid and/or isocitric acid can be adopted and used. Hyperfiltration of fermentation solutions is effected according to the present invention after conventionally purifying and separating said solutions from cell fragments and suspended particles, for instance, by ordinary filtration, centrifuging, and/or column chromatography. If dissolved macromolecular components, for instance, proteins, or polysaccharides are present in said solutions, it is sometimes advisable to subject the filtered, centrifuged, and/or chromatographed solutions to ultrafiltration. Such ultrafiltration can be effected with conventional porous membranes and at a working pressure of up to about 10 bars.

If citrates and/or isocitrates are to be separated from a solution of a pH-value of 5.5 to 7.5 which has been preliminarily purified in this manner as it is, for instance, obtained on producing citric acid by fermentation, by means of yeasts, of carbohydrates or hydrocarbons, it is the preferred procedure to use, according to the present invention, membranes with acid groups of a swelling power of between about 5% and about 25%, by volume, and advantageously of a swelling power of between about 8% and about 18%, by volume, and the permfiltration is effected at a pressure between about 30 bars and about 100 bars. Under these conditions the citrate and/or isocitrate is retained predominantly by the membrane while the other components of the solution permeate through the membrane.

When using the same membranes for purifying citric acid solutions of a pH-value below 3.0 and at a pressure between 5 bars and 50 bars, conversely the accompanying components are retained by the membrane and the citric acid and/or isocitric acid permeates.

It is also possible to use membranes according to the present invention with basic groups and a swelling power of about 3% to about 15%, by volume, and preferably of about 5% to about 10%, by volume, for citric acid-containing solutions of a pH-value under 3.0 and at a pressure of about 30 bars to about 100 bars. In this case the citric acid and/or isocitric acid is retained predominantly and the other constituents of the starting solution permeate.

It has also been found that it is possible according to the present invention to first adjust a fermentation solution of a pH of about 5.5 to about 7.5 to a pH below 3.0 by the addition of polyvinyl sulfonic acid whereafter the thus adjusted solution is further processed by means of a membrane having acid groups.

Acidifying with polyvinyl sulfonic acid has the advantage that said polymeric strong acid is retained by the membrane and that thus citric acid and/or isocitric acid which permeate through the membrane are not contaminated therewith. The dissolved polyvinyl sulfonic acid, furthermore, does not absorb any component of the solution as this is frequently the case when using granulated solid ion exchange agents. With polyvinyl sulfonic acid, acidifying and separation can be carried out in one single reaction step. A further essential advantage of using polyvinyl sulfonic acid for acidifying citric acid or citrate solutions is that no additional salt enrichment, for instance, with inorganic salts formed by conventional acidification takes place. Such additional salt formation would impair the separation effect of the membrane.

When using, for instance, sulfuric acid, in place of polyvinyl sulfonic acid, 1.5 moles of sodium sulfate are produced from 1 mole of trisodium citrate. If, for instance, the free citric acid shall permeate through the membrane while the sulfate shall be retained by the membrane, the high sulfate concentration in the solution as it has been caused by such acidification with sulfuric acid, results in a much lower retention power of the membrane with respect to sulfate and thus to a poorer separation factor. This impairment in the separation effect is not observed when acidifying with polyvinyl sulfonic acid.

It is also possible according to the present invention to combine the permselective membranes with acid groups with permselective membranes with basic groups in subsequent separation steps. As a result thereof further possibilities of separating and concentrating citric acid and/or isocitric acid are achieved. For instance, the membranes with acid groups according to the present invention can be used for separating citric acid and/or isocitric acid from an acid fermentation broth, preferably at a pH of about 1.0 to about 3.0, and a medium working pressure, preferably at a pressure of about 5 bars to about 50 bars. In this case citric acid and/or isocitric acid permeate through the membrane while at the same time the inorganic salts are partially retained and the macromolecular components of the fermentation broth are completely retained. The citric acid and/or isocitric acid separated by such a separation step from the fermentation broth is supplied at the same pH range to a subsequent second hyperfiltration step using a membrane with basic group according to the present invention. Citric acid and/or isocitric acid are retained in this step at a high working pressure, preferably at a pressure of about 30 bars to about 100 bars. They are thus concentrated while the inorganic salts predominantly permeate the membrane.

In this manner partial separation of citric acid and/or isocitric acid from the accompanying salts is achieved in both hyperfiltration steps, namely:

In the first step by separating from the fermentation broth citric acid and/or isocitric acid which pass through the membrane and In the second step by retaining said acids and concentrating the same.

This second separation step can also be carried out at a slightly acid to alkaline pH-range, preferably at a pH of about 5.5 to about 7.5. In this case concentration of the solution in the second step must be effected with membranes having acid groups.

Polycondensation products such as polyimides and polyamides which are modified with acid and basic groups are membranes useful in the process according to the present invention. The polyimides are produced by dehydration of polyamide carboxylic acids either thermally or by means of dehydrating reagents such as acetic acid anhydride. The polyamide carboxylic acids and polyamides are synthesized by polycondensation of multifunctional carboxylic acids such as, for instance, pyromellitic acid, trimellitic acid, terephthalic acid, naphthalene dicarboxylic acid, with aromatic diamines, such as, for instance, 4,4'-diamino diphenyl methane, p-phenylene diamine, 3,5-diamino benzoic acid, and others. The polycondensation is effected in a known manner, for instance, according to U.S. Pat. No. 3,179,614 or U.S. Pat. No. 3,094,511.

The acid and basic groups are introduced into said polycondensation products either by using corresponding substituted diamines or by reacting the polycondensation products with acid or basic reagents. As acid substituents there are suitable, according to the present invention, preferably sulfonic acid, carboxylic acid, and/or phosphonic acid groups, and as basic substituents preferably primary, secondary, and/or tertiary amino groups. Introduction of these substituents into the polycondensation products can be effected by reacting functional groups which are already present in the diamine component, for instance, by esterifying a carboxyl group with p-phenol sulfonic acid or tartaric acid or by amide formation with diethylamino propylamide. Free amino groups can furthermore be introduced, for instance, by cross-linking the polycondensation products with di-isocyanates, whereby residual isocyanate groups react with water to form the amino group.

In accordance with the present invention there can also be used membranes composed of vinyl copolymers modified by acid or basic groups, for instance, of styrene, acrylonitrile, acrylic acid, itaconic acid, vinylsulfonic acid, vinylpyridine, or butadiene.

Substituted polyalkylenes and especially polyethylenes, polybenzimidazoles, copolymers of perfluoro ethylene and propylene, cellulose, polyvinyl alcohol, aromatic or aliphatic polyethers, poly-electrolyte complex polymers, and others can also be used although the polyimides and polyamides have proved to be the most effective membrane materials.

The basic and acid groups are either introduced via the monomers, for instance, vinyl sulfonic acid, vinylpyridine, or by reacting the copolymers, for instance, by sulfonating styrene or by quarternizing substituted amino groups attached to styrene. Aromatic polysulfones which are substituted by sulfonic acid groups form also suitable membranes.

Copolymerization and preparation of the polysulfones are known to the art and, therefore, are not described herein in detail. See, for instance, Kirk-Othmer "Encyclopedia of Chemical Technology" 2nd edition, vol.16, pp. 272-281.

Of great importance with respect to the excellent separation power of the various permselective membranes according to the present invention is their swelling power. Said power is dependent upon the number of the acid of basic groups introduced into the molecule and must be with membranes substituted by acid groups between about 5% and about 25%, by volume, and preferably between about 8% and about 18%, by volume, and with basically substituted membranes between about 3% and about 15%, by volume, and preferably between about 5% and about 10%, by volume.

It is highly surprising that only membranes exhibiting such a swelling power possess the excellent separation effectiveness observed. The swelling power is determined by drying the moist membrane over silica gel (TM. BLAUGEL) in the exsiccator. The loss in volume indicates the swelling power.

The polymers can be worked up to form membrane bodies with flat, tubular, helical, and hollow fiber-shaped membranes when producing the membranes.

The membranes may have a homogeneous as well as an asymmetric macrostructure. By "asymmetric macrostructure" there is understood a membrane with non-uniform pores, i.e. a membrane which has on its one side large pores while the pore size decreases towards the opposite side. Such an asymmetric macrostructure is frequently of importance with regard to a superior flux rate.

DESCRIPTION OF THE PREFERRED EMBODIMENTS

The following examples serve to illustrate the preparation of membranes of selective permeability which are useful for carrying out the process according to the present invention of separating citrate or, respectively, citric acid and/or isocitric acid in their aqueous solutions from other accompanying components.

EXAMPLE 1

Copolymer membrane of vinylsulfonic acid and acrylonitrile 1 : 6

Seven g. of acrylonitrile, 2 ml. of dimethylsulfoxide, 0.24 g. of potassium persulfate ($K_2S_2O_8$), and 0.01 g. of sodium bisulfite are added to 100 g. of an aqueous solution of 25%, by weight, of vinylsulfonic acid sodium (as supplied by the firm Hoechst A.G.). The mixture is adjusted to a pH of 1.0 and is caused to polymerize by keeping it at 5° C. for 48 hours. Thereafter, the reaction product is precipitated by the addition of methanol and is washed therewith. Further washing is effected with water. The product is then dissolved in N-methylpyrrolidone in the cold. A solution of 10%, by weight, of the polymer is spread at room temperature by means of a 200 μm. doctor blade or squeegee on a polished glass plate. The resulting film is dried for two hours in a vacuum.

| | |
|---|---|
| Thickness of the film: | 5 μm. |
| Resistance to tearing (in moist condition at 20° C., while pulling off 30 mm./min.): | 266 kg./sq.cm. |
| Swelling power (after storing the membrane for 24 hours at 20° C. in water and drying in a exsiccator): | 10% by volume |
| Capacity (in moistened condition): | 1.4 mVal/g. of membrane |
| (mVal = milliequivalents) | |

The resistance to tearing is determined according to DIN specification for plastics.

The capacity in moistened condition is the content of the moist membrane of acid or basic groups. To determine the capacity, the moist membrane is titrated with 0.1 N sodium hydroxide solution or with 0.1 N sulfuric acid solution. The capacity of the membrane as given in Example 1 of 1.4 mVal/g. of membrane indicates that 1 g. of the moist membrane requires 1.4 mVal. of sodium hydroxide.

EXAMPLE 2

Sulfonated polyimide membrane

A 5% solution of a polyamide carboxylic acid prepared from pyromellitic acid di-anhydride and 3.5-diamino benzoic acid in dimethylformamide ($\mu_{inh.}$ = 1.80 dl./g.) is spread on a polished glass plate by means of a 100 μm. doctor blade or squeegee. The resulting film is left for about 3 hours in a vacuum at room temperature and is then placed for 80 hours into a mixture of acetic acid anhydride and pyridine (proportion by volume: 1 : 1) at about 25° C. The polyimide membrane is then removed from the glass plate carrier and is treated at 60° C. in a mixture of dimethylformamide, pyridine, and thionylchloride (proportion by volume: 5 : 45 : 50) for 30 minutes. The membrane is then heated at 60° C. in dimethylformamide with 1%, by weight, of completely dried 2,3-dihydroxy napthalene-6-sulfonic acid sodium (or p-phenol sulfonic acid sodium) for two hours and is stored in water.

| | |
|---|---|
| Thickness of the film in moistened condition | 16.5 μm. |
| Swelling power (after storing the film at 20° C. in water for 24 hours): | 16% by volume |
| Capacity (in moistened condition): | 0.30 mVal/g. of membrane |

$\mu_{inh.}$ = 1.80 dl./g. as given hereinabove designates the "inherent viscosity" of the solution. The inherent viscosity $\mu_{inh.}$ is characterized by the following equation:

$$\mu_{inh.} = \frac{\ln \text{relative viscosity}}{\text{concentration in g./dl.}} = 1.80 \text{ dl./g.}$$

In said equation ln indicates the natural logarithmus and dl. indicates deciliter or 100 ml.

In the above given Example 2 dimethylformamide in the mixture of dimethylformamide, pyridine, and thionylchloride serves as solvent, thionylchloride converts the carboxyl groups into carboxylic acid chloride groups, and pyridine combines and binds the hydrochloric acid formed thereby. The carboxylic acid chloride groups are then modified by the reaction with 2,3-dihydroxy naphthalene6-sulfonic acid sodium whereby they react with the hydroxyl groups of the naphthalene sulfonic acid compound to form the polyimide polymer membrane containing the sulfo groups of the naphthalene sulfonic acid reactant.

It is advisable to store the membrane obtained according to Example 2 in water, since it becomes brittle with the formation of cracks and fissures if stored in dry condition.

EXAMPLE 3

Sulfonated membrane of the copolymer of styrene and 1,3-butadiene in the proportion of 3 : 1

0.08%, by weight, of ferrous sulfate, 0.04%, by weight, of dibenzoyl peroxide, and 3%, by weight, of sodium laurylsulfate are dissolved in water in a pressure resistant bottle. 20%, by weight, of styrene and 10%, by weight, of 1,3-butadiene are added thereto. The mixture is allowed to stand in a nitrogen atmosphere at 25° C. for 7 hours while shaking it initially. The resulting latex is precipitated by means of methanol, 1%, by weight, of concentrated hydrochloric acid, and 0.1%, by weight, of N-phenyl-2-naphthylamine which serves as stabilizer to prevent oxidative attack on the latex. The precipitated copolymer is washed and is dried in a vacuum at room temperature. A solution with 10%, by weight, of the resulting copolymer in tetrahydrofuran is spread by means of a 200 μm. doctore blade or squeegee on a polished glass plate. The resulting membrane is air-dried. It is placed for crosslinking into a 5%, by volum, solution of freshly distilled sulfurmonochloride ($S_2Cl_2$) in dry nitromethane. After standing for 2 hours at room temperature, it is washed in n-heptane containing 10%, by weight, of carbon disulfide and is removed from the glass plate by immersing the plate with the film in methanol and water. After causing the membrane to swell in chloroform, it is sulfonated in a solution of 2%, by volume, of chloro sulfonic acid ($ClSO_3H$) in chloroform at room temperature within 15 minutes. The sulfonated membrane is then washed successively with chloroform, methanol, and water.

| | |
|---|---|
| Thickness of the film | 20 μm. |
| Swelling power (by storing in water at 20° C. for 24 hours): | 12%, by volume, |
| Capacity (in moistened condition): | 1.8 mVal./g. of membrane |

EXAMPLE 4

Copolymer membrane of vinyl sulfonic acid and acrylonitrile in the proportion of 1 : 3

A copolymer membrane of vinyl sulfonic acid and acrylonitrile in the proportion of 1 : 3 is produced according to Example 1 with the addition of 5%, by weight, of acrylic acid and by polymerization at 60° C. The membrane is treated in 2.5%, by volume, of toluylene di-isocyanate which serves as cross-linking agent in xylene at 40° C. for 30 minutes and is washed with xylene.

| | |
|---|---|
| Thickness of the film: | 11 μm. |
| Swelling power (by storing in water at 20° C. for 24 hours): | 15%, by volume, |
| Capacity (in moistened condition) | 2,3 mVal./g. of membrane. |

EXAMPLE 5

Carboxylated polyimide membrane

A polyimide membrane is produced according to Example 2 and is treated with 5%, by weight, of strongly dried L(+)-tartaric acid in dimethylformamide at 60° C. for 20 hours. The resulting membrane is stored in water.

| | |
|---|---|
| Thickness of the film: | 15 μm. |
| Swelling power (by storing in water at 20° C. for 24 hours): | 18%, by volume |
| Capacity (in moistened condition) | 0.7 mVal./g. of membrane. |

EXAMPLE 6

Sulfonated polysulfone membrane

A solution of 15%, by weight, of polysulfone, sold under the trademark PSF-3500 by Union Carbide, in 1,2-dichloro ethane is introduced together with a solution of 5%, by volume, of chlorosulfonic acid ($ClSO_3H$) in 1,2dichloro ethane in equal proportions, by volume, into 1,2dichloro ethane. The mixture is stirred at 60° C.

for 5 hours. The precipitated polymer is dissolved in dimethylformamide, precipitated with acetone, washed, and dried at 60° C. in a vacuum. A 10%, by weight, solution of the polymer in dimethylformamide is spread on a glass plate by means of a 200 μm. doctor blade or squeegee. The resulting membrane is dried in a vacuum.

| | |
|---|---|
| Thickness of the film: | 12 μm. |
| Swelling power (on storing in water at 20° C. for 24 hours): | 14%, by volume, |
| Capacity (in moistened condition): | 1.2 mVal./g. of membrane |
| Tensile strength in moist condition: | 80 kg./sq.cm. |

EXAMPLE 7

Copolymer membrane of 2-vinyl pyridine and 1,3-butadiene in the proportion of 2 : 1

2-Vinyl pyridine are filled into a glass tube under nitrogen with 0.2 mole % of azo-isobutyric acid nitrile. The mixture is degasified. 33 mole % of 1,3-butadiene are introduced into said mixture by distillation. The tube is then sealed and is allowed to stand at 50° C. for 24 hours. The resulting polymer is dissolved in tetrahydrofuran containing 0.2%, by weight, of N-phenyl-2-naphthylamine serving as anti-oxidative stabilizer and is precipitated by the addition of n-hexane, washed, and dried in a vacuum.

A 10%, by weight, solution of the copolymer in tetrahydrofuran is spread on a polished glass plate by means of a 200 μm. doctor blade or squeegee. The glass plate with the resulting membrane is dried in a vacuum at 70° C. for one hour. Gaseous methyl bromide is introduced into the vacuum dryer and the membrane is allowed to stand at 70° C. in said methyl bromide atmosphere for 48 hours. It is then placed into a 5%, by volume, solution of freshly distilled sulfur monochloride ($S_2Cl_2$) in dry nitromethane. After allowing the membrane to stand therein for 6 hours at room temperature, it is washed in n-heptane with 10%, by volume, of carbon disulfide and is removed from the glass plate by placing it in methanol and water.

| | |
|---|---|
| Thickness of the film: | 26 μm. |
| Swelling power (by storing in water at 20° C. for 24 hours): | 8%, by volume, |
| Capacity (in moistened condition): | 1.2 mVal./g. of membrane. |

EXAMPLE 8

Polyimide membrane containing amino groups

A polyimide membrane obtained according to Example 2 is treated at 100° C. in dimethylformamide with 3%, by weight, of 4,4-diphenylmethane di-isocyanate for 3 hours. The membrane is then rinsed with acetone and dried.

| | |
|---|---|
| Thickness of the film: | 16 μm. |
| Swelling power (by storing in water at 20° C. for 24 hours): | 5%, by volume, |
| Capacity (in moistened condition) | 0.1 mVal./g. of membrane. |

EXAMPLE 9

Preparation of polyvinyl sulfonic acid 1,800 g. of vinyl sulfonic acid sodium (25%, by weight, aqueous solution, sold by Hoechst A.G.) are polymerized at 5° C. to a solution of low viscosity within 48 hours (Redox system potassium persulfate ($K_2S_2O_8$)/sodium bisulfite ($NaHSO_3$)). The polymer is precipitated by adding the reaction mixture to about 3,600 ml. of methanol and the precipitate is filtered off by suction. 330 g. of the moist precipitate are twice dissolved in water and precipitated with methanol. A solution of the sodium salt in 6,000 ml. of water is converted into the free acid by passing it through the ion exchange agent sold under the trademark Amberlite IR-120. The eluate is freed by hyperfiltration by means of a membrane obtained according to Example 6 from low-molecular portions and is concentrated by evacuation in a vacuum. The resulting yellowish brown, strongly viscous solution (333 g.) containing the polyvinyl sulfonic acid is analyzed titrimetrically and 19.6%, by weight, of the free acid are determined therein.

It has been found that, in order to separate the citrate from solutions of a pH of about 5.5 to about 7.5 and at a pressure of about 30 bars to about 100 bars, there are especially useful the membranes produced according to Examples 1, 3, and 4, while at an acid range under a pressure of about 5 bars to about 50 bars the membranes produced according to Examples 2, 5, and 6 are suitably employed. Of course, it is possible to use all the above mentioned membranes in each mode of operation.

The membranes with basic groups are preferably employed after the citric acid has permeated the membranes containing acid groups according to the present invention in order to concentrate the citric acid in a second step in the acid range. Especially suitable for this purpose are membranes obtained according to Examples 7 and 8.

The following Tables, I, II, and III show the excellent separating effect of the membranes according to the present invention in comparison with membranes according to the state of the art. As a measure for the effectiveness of the membranes there was determined the retention power (R) and the separation factor (SF), i.e. the quotient of the ratio of concentration in the starting solution to the ratio of concentration in the permeated solution.

$$SF = \frac{\text{Concentration quotient in the starting solution}}{\text{Concentration quotient in the permeated solution}}$$

$$\text{Concentration quotient} = \frac{\text{Citrate concentration}}{\text{Phosphate or sulfate concentration}}$$

Membranes with acid groups according to the present invention were used in the tests of Table I. The pH-value of the solution was 7.1. According to the present invention citric acid and/or isocitric acid predominantly were retained and the other components of the solution permeated. The solution was passed through the membrane at a velocity of flow of 12 cm./second and the temperature was 20° C.

Table II shows the separation effect of the membranes with acid groups according to the present invention at pH-values below 3.0 whereby according to the invention citric acid and/or isocitric acid permeated predominantly while the other components of the starting solution were retained. The temperature was 20° C.

Membranes with basic groups according to the present invention were used in the tests of Table III at a pH-value below 3.0. According to the present invention citric acid and/or isocitric acid were retained while the other components permeated. The temperature amounted to 20° C.

Table I

Retention power (R) and separation factor (SF) of the membranes according to the present invention (Tests 1 to 6) as well as membranes according to the state of the art (Tests 7 to 9)
TSC = trisodium citrate    pH = 7.1

| Test No. | Membrane | Starting solution | Pressure atmosphere | Rate of flow l./sq.m./day | | R | SF |
|---|---|---|---|---|---|---|---|
| 1.) | Copolyvinylsulfonate-acrylonitrile (Example 1) | 1.5 N TSC 0.01 N KH$_2$PO$_4$ 0.01 N CaSO$_4$ | 40 | 23 | Citrate Sulfate Phosphate | 91% 12% 31% | — 9.8 7.7 |
| 2.) | Copolyvinylsulfonate-acrylonitrile (Example 1) | 1.5 N TSC 0.01 N KH$_2$PO$_4$ 0.01 N CaSO$_4$ | 100 | 174 | Citrate Sulfate Phosphate | 99% 64% 91% | — 36.0 9.0 |
| 3.) | Polyimide sulfonated (Example 2) | 1.5 N TSC 0.01 N KH$_2$PO$_4$ 0.01 N MgSO$_4$ | 100 | 220 | Citrate Phosphate Sulfate | 91% 63% 63% | — 4.1 4.1 |
| 4.) | Copolymer of styrene-1,3-butadiene (sulfonated (Example 3) | 1.5 N TSC 0.2 N K$_2$SO$_4$ 0.01 N KH$_2$PO$_4$ | 40 | 25 | Citrate Sulfate Phosphate | 91% −18% 30% | — 13.1 7.8 |
| 5.) | Copolyvinylsulfonate-acrylonitrile (Example 1) | Fermentation solution 5.3%, by weight, of citrate 4.8%, by weight, of isocitrate 0.049%, by weight, of KH$_2$PO$_4$ 0.079%, by weight, of CaSO$_4$ pH 6.5 | 40 | 20 | Citrate Isocitrate Sulfate Phosphate | 85% 88% 35% 54% | — — 4.2 3.1 |
| 6.) | Polyimide (sulfonated) (Example 2) | Fermentation solution as used in Test 5 | 40 | 35 | Citrate Sulfate Phosphate | 76% 2% 42% | — 4.1 2.4 |
| 7.) | Cellulose acetate tempered at 85° C. | as in Test 4 | 40 | 25 | Citrate Sulfate Phosphate | 96% 99% 94% | — 0.3 1.5 |
| 8.) | Carboxymethyl cellulose | as in Test 4 | 40 | 25 | Citrate Sulfate Phosphate | 23% 10% 14% | — 1.2 1.1 |
| 9.) | Polyelectrolyte (sulfonated) sold under the trademark "AMICON UM-05" | as in Test 1 | 7 | 11 | Citrate Sulfate Phosphate | 17% −22% 10% | — 1.5 1.3 |

REMARKS:
The minus values given in column "R" hereinabove indicate a so-called "negative retention power", i.e. the concentration of the respective compound is increased in the permeated solution with respect to the starting solution.

Table II

Retention power (R) and separation factor (SF) of the membranes according to the present invention (Tests 1 to 6) as well as membranes according to the state of the art (Tests 7 to 9)

| Test No. | Membrane | Starting Solution | pH | Pressure atm. | Velocity of flow cm./sec. | Rate of flow l./sq.m. day | | R | SF |
|---|---|---|---|---|---|---|---|---|---|
| 1.) | Polyimide (sulfonated) (Example 2) | 1.5 N Citric acid 0.03 N KH$_2$SO$_4$ 0.02 N K$_2$SO$_4$ | 1.9 | 30 | 6 | 255 | Citric acid Phosphate Sulfate | 19% 31% 58% | — 0.86 0.49 |
| 2.) | Polyimide (carboxylated) (Example 5) | 1.5 N Citric acid 0.02 N KH$_2$PO$_4$ | 2.0 | 40 | 6 | 400 | Citric acid Phosphate | 5% 42% | — 0.63 |
| 3.) | Copolyvinylsulfonate-acrylonitrile (Example 4) | 1.5 N Citric acid 0.01 N MgSO$_4$ | 1.9 | 30 | 6 | 1900 | Citric acid Sulfate | 11% 46% | — 0.61 |
| 4.) | Polysulfone (sulfonated) (Example 6) | 2.0 N Citric acid 0.01 N MgSO$_4$ 0.01 N KH$_2$PO$_4$ | 1.7 | 30 | 10 | 87 | Citric acid Phosphate Sulfate | 31% 45% 72% | — 0.80 0.41 |
| 5.) | Polyimide (sulfonated) (Example 2) | Fermentation solution pH 6.5 Citrate 5.3%, by weight, isocitrate 4.8%, by weight, KH$_2$PO$_4$ 0.049%, by weight, CaSO$_4$ 0.079%, by weight, acidified by means of polyvinylsulfonic acid | 2.0 | 30 | 6 | 145 | Citric acid Isocitric acid Phosphate Sulfate | −23% −28% 10% 25% | — — 0.73 0.61 |
| 6.) | Polysulfone (sulfonated) (Example 6) | as in Test 5 acidified with polyvinylsulfonic acid | 2 | 30 | 6 | 84 | Citric acid Phosphate Sulfate | −18% 15% 33% | — 0.72 0.57 |
| 7.) | Cellulose acetate tempered at 70° C. | as in Test 1 | 1.9 | 30 | 6 | 87 | Citric acid Sulfate | 22% 23% | — 0.99 |
| 8.) | Carboxymethyl cellulose | as in Test 1 | 1.9 | 30 | 6 | 87 | Citric acid Sulfate Phosphate | 32% 35% 25% | — 0.96 1.10 |
| 9.) | Polyelectrolyte (sulfonated) Sold under the trademark "AMICON UM-05" | as in Test 4 | 1.9 | 7 | 6 | 1200 | Citric acid Sulfate Phosphate | 5% −5% 1% | — 1.11 1.04 |

Table III

Retention power (R) and separation factor (SF) with membranes according to the present invention (Tests 1 and 2) as well as with a membrane according to the state of the art (Test 3)

| Test No. | Membrane | Starting solution | pH | Pressure atm. | Velocity of flow cm./sec. | Rate of flow l./sq.m. day | R | | SF |
|---|---|---|---|---|---|---|---|---|---|
| 1.) | Copolymer of 2-vinyl-pyridine and 1,3-butadiene in the proportion of 2:1 (Example 7) | 1.5 N Citric acid 0.01 N KH$_2$PO$_4$ 0.01 N CaSO$_4$ | 1.9 | 100 | 21 | 15 | Citric acid Phosphate Sulfate | 91% 64% 78% | — 4.0 2.4 |
| 2.) | Polyimide (aminated) (Example 8) | 1.0 N Citric acid 0.02 N KH$_2$PO$_4$ 0.01 N K$_2$SO$_4$ | 2.2 | 100 | 12 | 31 | Citric acid Phosphate Sulfate | 97% 84% 89% | — 5.3 3.7 |
| 3.) | Cellulose acetate (tempered at 85° C.) | as in Test 1 | 2.2 | 100 | 12 | 31 | Citric acid Phosphate Sulfate | 96% 94% 99% | — 1.5 0.3 |

EXAMPLE 10

An acid fermentation broth of the pH of 2.0 with 10.1%, by weight, of citric acid and isocitric acid and 0.129%, by weight, of inorganic salts (potassium monophosphate and magnesium sulfate) is passed at a working pressure of 30 bars with a velocity of flow of 12 cm./second over 1 sq.m. of a membrane obtained according to Example 4 in a tubular hyperfiltration cell. The membrane shows no retention power for citric acid and isocitric acid, but it retains about 20% of the inorganic salts. 101 kg. of citric acid and isocitric acid are present in 1 cu.m. of permeated solution after 16 hours in addition to 1.03 kg. of inorganic salts. The yield of citric acid and isocitric acid is 100% in this first hyperfiltration step while the amount of salts is reduced by about 20%.

The permeated solution is then discontinuously introduced into a second hyperfiltration cell with 1 sq.m. of membrane produced according to Example 7 and is circulated under a working pressure of 100 bars with a velocity of flow of 30 cm./second.

In this case the membrane shows a retention power against citric acid and isocitric acid of 99.8% with a retention power against inorganic salts of about 90%. At a water yield of 0.85 (volume of permeated solution/volume of starting solution) there are retained 99.87 kg. of citric acid and isocitric acid and 0.66 kg. of inorganic salts in 0.15 cu.m. of concentrated solution after 72 hours.

Thus, a yield of citric acid and isocitric acid of about 99% is obtained with a loss of about 50% of the inorganic salts while the solution is concentrated about six times.

It is understood that all soluble metal salts of citric acid and/or isocitric acid can be separated from other organic compounds and inorganic salts by the process according to the present invention. Thus not only the alkali metal salts but also other water soluble salts such as, for instance, ferrous citrate, ferric citrate, ammonium-ferric citrate, calcium-alkali metal citrates, magnesium-alkali metal citrates, and others can be separated and concentrated.

Of course, many changes and variations in the starting solutions and their citric acid and/or isocitric acid content and their content of organic and inorganic accompanying components, in the composition of the membranes with acid and basic groups of selective permeability, in their preparation, in the hyperfiltration conditions such as velocity of flow, rate of flow, pH-value, working pressure, and the like may be made by those skilled in the art in accordance with the principles set forth herein and in the claims annexed hereto.

We claim:

1. A process of separating a material selected from citric acid, isocitric acid, their salts, and mixtures of such materials, present in an aqueous starting solution, especially a fermentation solution, from impurities comprising other organic compounds or inorganic salts in said solution, comprising the step of contacting the starting solution with a permselective membrane comprising a. a polymer containing chemically bound acid groups in a proportion such that the swelling power of the polymer is between about 5% and about 25%, by volume, or
   b. a polymer containing chemically bound basic groups in a proportion such that the swelling power of the polymer is between about 3% and about 15%, by volume, at a pH-value between about 0.1 and about 8.0 and under a pressure between about 5 bars and about 100 bars for the acidic polymers (a) and at a pH-value between about 1.0 and 3.0 and under a pressure between about 30 bars and about 100 bars for the basic polymers (b) whereby a permeate solution and a retention solution result on opposite sides of said membrane, one of said resulting solutions having a substantially higher ratio of said material to said impurities than in said starting solution.

2. The process of claim 1, wherein the starting solution is contacted at a pH-value between about 5.5 and about 7.5 and under a pressure between about 30 bars and about 100 bars with a membrane comprised of said acidic polymer (a), whereby said material is selectively retained by said membrane in the retention solution, and said other organic compounds and inorganic salts pass through said membrane in the permeate solution.

3. The process of claim 1, wherein the starting solution is contacted at a pH-value between about 1.0 and about 3.0 and under a pressure between about 5 bars and about 50 bars with a first membrane comprised of said acidic polymer (a), whereby said material passes through said membrane in the permeate solution and said other organic compounds and inorganic salts are selectively retained by said membrane in the retention solution.

4. The process of claim 1, wherein the starting solution is contacted at a pH-value between about 1.0 and about 3.0 and under a pressure between about 30 bars and about 100 bars with a membrane comprised of said basic polymer (b), whereby said material is selectively retained by said membrane in the retention solution and said other organic compounds and inorganic salts pass through said membrane in the permeate solution.

5. The process of claim 3, wherein the starting solution is first adjusted to a pH-value between about 1.0 and about 3.0 by the addition of polyvinylsulfonic acid and thereafter subjected to the process of claim 13.

6. The process of claim 3, further comprising the step of contacting said resulting permeate solution at a pH-value between about 1.0 and about 3.0 and under a pressure between about 30 bars and about 100 bars with a second membrane comprised of said basic polymer (b), whereby said material is selectively retained by said second membrane in the retention solution thereof.

7. The process of claim 1, wherein said permselective membrane comprises a. a polymer selected from polyimides, polyamides, polysulfones, and vinyl polymers, and containing chemically bound acid groups in a proportion such that the swelling power of the polymer is between about 5% and about 25%, by volume, or b. a polymer selected from polyimides, polyamides, and vinyl copolymers, and containing chemically bound basic groups in a proportion such that the swelling power of the polymer is between about 3% and about 15%, by volume.

8. The process of claim 7, wherein said acid groups are selected from the group consisting of sulfonic acid groups, carboxylic acid groups and phosphonic acid groups, and wherein said basic groups are selected from the group consisting of primary, secondary and tertiary amino groups.

9. The process of claim 7, wherein the membrane comprises a polyimide or a polyamide containing said acid or basic groups.

10. The process of claim 7, wherein the membrane comprises a polysulfone containing said acid groups.

11. The process of claim 7, wherein the membrane comprises a vinyl copolymer containing said acid or basic groups.

12. The process of claim 1, further comprising, prior to said contacting step, the step of removing suspended particles from said starting solution.

13. The process of claim 1, further comprising, prior to said contacting step, the step of ultrafiltering said starting solution to remove dissolved macromolecular components therefrom.

14. The process of claim 1, wherein said permelective membrane is comprised of a polymer selected from the group consisting of: (a) a copolymer of vinylsulfonic acid and acrylonitrile in a ratio of 1:6; (b) sulfonated polyamide; (c) a sulfonated copolymer of styrene and 1,3-butadiene in a ratio of 3:1; (d) a copolymer of vinyl sulfonic acid and acrylonitrile in a ratio of 1:3; (e) a carboxylated polyimide; (f) a sulfonated polysulfone; (g) a copolymer of 2-vinyl pyridine and 1,3-butadiene in a ratio of 2:1; (h) a polyimide containing amino groups; and (i) polyvinylsulfonic acid.

15. The process of claim 1, wherein the swelling power of polymer (a) is between about 8% and about 18%, by volume, and the swelling power of polymer (b) is between about 5% and about 10%, by volume.